US00PP08447P

United States Patent [19]

Stoots

[11] Patent Number: Plant 8,447

[45] Date of Patent: Nov. 2, 1993

[54] VARIETY OF GERANIUM NAMED 'MEDALLION DARK RED'

[75] Inventor: Eleanor Stoots, Connellsville, Pa.

[73] Assignee: Oglevee, Ltd., Connellsville, Pa.

[21] Appl. No.: 957,620

[22] Filed: Oct. 6, 1992

[51] Int. Cl.[5] ..... A01H 5/00
[52] U.S. Cl. ..... Plt./87.12
[58] Field of Search ..... Plt./87.12

[56] References Cited

U.S. PATENT DOCUMENTS

P.P. 5,054 5/1983 Elsner ..... Plt. 87.12

*Primary Examiner*—James R. Feyrer
*Attorney, Agent, or Firm*—Webb, Burden, Ziesenheim & Webb

[57] ABSTRACT

The new variety 'Medallion Dark Red' is characterized by an intense red bloom, a controlled growth habit, rapid basal branching and prolific cuttings for propagation.

1 Drawing Sheet

BACKGROUND OF THE INVENTION

The present invention comprises a new and distinct cultivar of *Pelargonium*×*hortorum* known by the varietal name 'Medallion Dark Red' (Oglevee No. 8069, Breeder No. EL-32-88). The new variety was discovered in a selected breeding program in Connellsville, Pa. on Jul. 19, 1988. The new variety is a selection from the crossing of the female parent 'Sunbelt Dark Red' (unpatented) and the male parent 'Veronica' (U.S. Plant Pat. No. 5,054). The new variety was first asexually reproduced by cuttings at Oglevee, Ltd. in Connellsville, Pa. on Jan. 24, 1989. The new variety has been asexually reproduced by cuttings at Oglevee, Ltd. in Connellsville, Pa. over a several year period. It has also been trial and field tested at Connellsville and has been found to retain its distinctive characteristics through successive propagations.

The new variety has the dark red bloom of the variety 'Sunbelt Dark Red' and the medium green foliage and compact habit of the variety 'Veronica'. The variety 'Sunbelt Dark Red' has a larger growth habit and the variety 'Veronica' has smaller foliage and a ligher color as compared with the new variety.

The cultivar when grown in a glass greenhouse in Connellsville, Pa. using natural light and 60° F. night, 68° F. day and 71° F. vent, has a response time of 6 weeks from a rooted cutting to flowering in a 10 cm. pot. The response time was determined on plants grown in soilless media employing constant fertilizer 200 parts per million of nitrogen and potassium in full light. The rooted cuttings were potted on Feb. 14, 1989 and flowered on Apr. 4, 1989.

DESCRIPTION OF THE DRAWING

FIG. 1 of the accompanying photographic drawing illustrates the new cultivar the color being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee, Ltd. in Connellsville, Pa. The plant history was taken on Jul. 8, 1992 using a plant which was grown in a 6" pot and blossomed under natural light in a greenhouse and the color readings were taken indoors under 200–220 foot candles of florescent cool white light. Color references are primarily to The RHS Colour Chart of The Royal Horticultural Society of London.

THE PLANT

Classification:
- *Botanical.*—*Pelargonium*×*hortorum.*
- *Commercial.*—Zonal florists' geranium.

Form: Compact mound form.
- *Height.*—20–21 cm above media surface.
- *Growth.*—Free and early flowering; basal branching.

Strength: Stands upright without artificial support.
Foliage: Stalked leaf attachment; slight zone present.
Leaves:
- *Size.*—7.0–9.5 cm across; fully expanded leaf.
- *Shape.*—Reniform; cordate base.
- *Margin.*—Crenate.
- *Texture.*—Slightly pubescent; slightly reflective.
- *Color.*—Top: Yellow/Green Group 146A. Bottom: Yellow/Green Group 146B.
- *Ribs and veins.*—Palmate Venation. Color: Yellow/Green Group 147C.

Petioles:
- *Color.*—Yellow/Green Group 146B.
- *Length.*—5.5–9.5 cm in length.

Stem:
- *Color.*—Yellow/Green Group 146C.
- *Internodes.*—1.0–2.5 cm.

THE BUD

Shape: Upright hemispherical cluster.
Size: 3.0–3.5 cm across.

INFLORESCENCE

Blooming habit: Semi-double; slow to shatter.
Size: 11.0–13.0 cm across, fully open bloom.
Borne: Umbel; florets on pedicel, pedicel on peduncle; 7.0–9.0 cm above foliage canopy.
Florets:
- *Form.*—Flat to slightly cupped; petaloids present.
- *Color.*—Top: Red Group 53C. Eye: Red Group 43B. Bottom: Red Group 47C.

*Petals.*—Margin entire; obovate; separate, not united; smooth, flat to slightly cupped; 6–9 in number.

*Size.*—3.5–4.5 cm across.

*Texture and appearance.*—Smooth; appearance from a distance is a bright magenta red with medium green foliage.

Petaloids:

*Quantity.*—1–3 in number.

*Shape.*—Flat; twisted some with pollen attached; some tubular.

*Color.*—Top: Red/Purple Group 57A. Bottom: Red Group 43C.

Pedicel:

*Length.*—3.0–4.0 cm.

*Color.*—Base: (peduncle end) Yellow/Green Group 146D. Tip: (stipule end) Red/Purple Group 59B.

Peduncle: Arises from the node opposite the leaf petiole; 15.0–17.0 cm in length.

*Color.*—Yellow/Green Group 146B.

Disease resistance: Not known.

Lasting quality: The flower has a good lasting quality of 10–14 days.

REPRODUCTIVE ORGANS

Stamens:

*Anthers.*—2.0–3.0 mm in length.

*Filaments.*—8.0–9.0 mm in length.

*Pollen.*—Golden brown.

Pistils:

*Number.*—One.

*Length.*—7.0–9.0 mm in length.

*Stigma.*—5–6 parted; red purple.

*Style.*—3.0–4.0 mm in length.

Ovaries: Superior; pubescent; pale green; 4.0–5.0 mm in length.

Fruit: None observed.

GENERAL CHARACTERISTICS

'Medallion Dark Red' brings to the geranium market the similar intense red bloom as 'Sunbelt Dark Red' but with a more controlled growth habit which is evident both indoors and in the garden. As well as providing a large show of color and a neat mound habit, this variety is very quick to basal branch providing a desirable amount of cuttings for production purposes when compared to 'Veronica'.

I claim:

1. A new and distinct variety of geranium plant, substantially as shown and described.

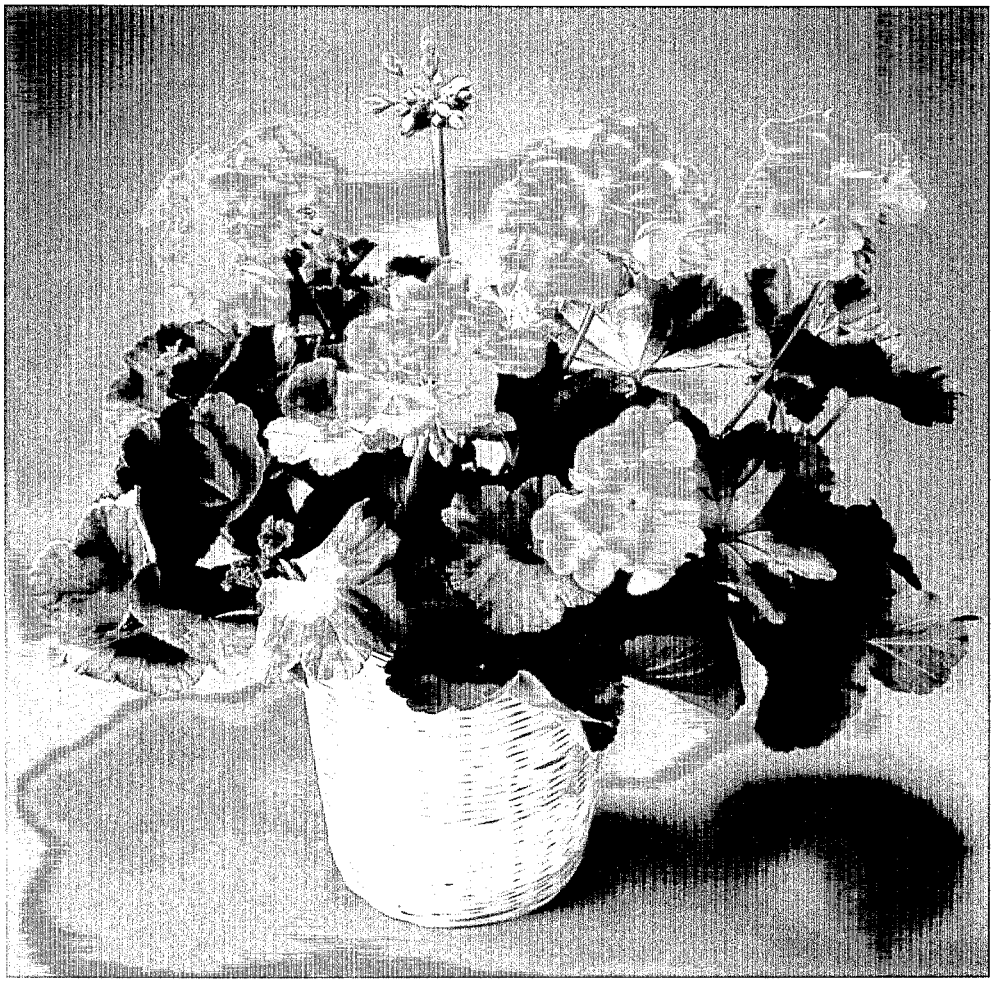

* * * * *